United States Patent [19]

Berthiaume et al.

[11] Patent Number: 5,339,833
[45] Date of Patent: Aug. 23, 1994

[54] SWIVEL EXCHANGE GUIDEWIRE

[75] Inventors: William A. Berthiaume, Hudson; Michel J. LeBlanc, Waltham, both of Mass.

[73] Assignee: C.R. Bard, Inc., Murray Hill, N.J.

[21] Appl. No.: 748,037

[22] Filed: Aug. 21, 1991

[51] Int. Cl.$^5$ ............................................. A61B 5/00
[52] U.S. Cl. .................................................... 128/772
[58] Field of Search ....................... 128/657, 658, 772; 604/95, 164, 170, 283

[56] References Cited

U.S. PATENT DOCUMENTS

| | | |
|---|---|---|
| 3,995,628 | 12/1976 | Gula et al. |
| 4,732,163 | 3/1988 | Bonello et al. ............... 128/772 |
| 4,798,598 | 1/1989 | Bonello et al. ............... 604/280 |
| 4,827,941 | 5/1989 | Taylor et al. ................. 128/657 |
| 4,846,193 | 7/1989 | Tremulis et al. ............. 128/772 |
| 4,860,757 | 8/1989 | Lynch et al. ................. 128/772 |
| 4,875,489 | 10/1989 | Messner et al. ............. 128/657 |
| 4,895,168 | 1/1990 | Machek ........................ 128/772 |
| 4,907,332 | 3/1990 | Christian et al. ............. 604/95 |
| 4,917,103 | 4/1990 | Gambale et al. ............. 128/772 |
| 4,922,923 | 5/1990 | Gambale et al. ............. 128/657 |
| 4,966,163 | 10/1990 | Kraus et al. .................. 128/772 |

FOREIGN PATENT DOCUMENTS 0347035 4/1989 European Pat. Off.

*Primary Examiner*—Max Hindenburg
*Attorney, Agent, or Firm*—Morgan & Finnegan

[57] ABSTRACT

An exchange length guidewire for use in percutaneous transluminal coronary angioplasty is formed in two sections including a proximal section and a distal section. The proximal end of the distal section is rotatably attached to the distal end of the proximal section so that it may be rotated freely with respect to the proximal section. The proximal section may be maintained in a coiled configuration in a storage hoop while the distal portion may be used as a steerable guidewire to assist in navigating a catheter to the intended vascular treatment site. When it is desired to perform a catheter exchange, the proximal section is removed from the storage hoop to permit the wire to extend to its full exchange length, typically slightly more than twice the length of the catheter. The catheter exchange then may be performed. Thereafter, the proximal section of the exchange wire may be reinserted into the storage hoop and while the distal portion may continue to serve as a steerable guidewire.

8 Claims, 4 Drawing Sheets

SWIVEL EXCHANGE GUIDEWIRE

FIELD OF THE INVENTION

This invention relates to guidewires for use with catheters in medical procedures such as in angioplasty.

BACKGROUND OF THE INVENTION

It has long been a common medical practice to use guidewires in the placement of catheters in a patient's blood vessels. With a guidewire in place in the blood vessel, a catheter can be threaded and advanced over the guidewire thus guiding the catheter to the intended vascular site. The guidewire serves to center the catheter within the blood vessel and reduces the risk of trauma to the blood vessel by the advancing catheter. The use of a guidewire also enables the catheter to be advanced through the blood vessel relatively quickly, thereby reducing the time required for the procedure.

A standard guidewire typically is slightly longer than the catheter with which it is to be used. For example, with an angiographic catheter of the order of 130 cm long, the guidewire typically may be of the order of 145 cm to 175 cm long. When the catheter is in place over the guidewire, a relatively short portion of the guidewire protrudes proximally from the catheter. That enables the guidewire to be manipulated, if desired, from its protruding proximal end. In that regard, it may be noted that the guidewire may be of a steerable construction in which a bend is formed in its distal tip and the direction in which the bent distal tip extends is controlled by rotating the guidewire from its proximal end. For example, the guidewire may be of the type described in U.S. Pat. No. 4,545,390.

In many vascular catheterization procedures, it may become necessary to change catheters during the procedure. Usually, it is preferred that the catheter be removed in a manner which enables a guidewire to remain in place in the blood vessel so that the next succeeding catheter in the procedure can be inserted into the blood vessel, over the guidewire to guide the catheter to the intended site in the blood vessel. In order to maintain a guidewire in place while withdrawing the catheter, the guidewire must be gripped at its proximal end to prevent it from being pulled out of the blood vessel together with the catheter. The catheter, however, is longer than the proximal portion of the guidewire which protrudes out of the patient. Thus, before the catheter is fully withdrawn, it completely covers the proximally extending end of the guidewire. As a result, a standard guidewire cannot be held in place to prevent it from being withdrawn together with the catheter.

Among the techniques for effecting a catheter exchange has been to use an exchange guidewire. The exchange guidewire typically is about 300 cm long, much longer than the typically standard guidewire. The structure of the standard and exchange wires typically is the same except for the length. The additional length of the exchange wire results in a long proximally protruding portion that is longer than the catheter to be removed. When the catheter is removed, some part of the proximally extending portion of the exchange wire will always be exposed to provide a means by which the exchange wire can be gripped and its position in the blood vessel maintained. Use of the exchange wire reduces the risk of trauma to the patient because it is placed while the first catheter remains in the patient. Thus, the procedure involves initial removal of the standard guidewire from the catheter while the catheter remains in place in the patient. Then the exchange wire is advanced through the catheter to replace the original guidewire. Because the exchange wire is guided through the patient's blood vessel by the first catheter, it does not contact the lumen of the blood vessel, except, perhaps, for a small portion which protrudes distally of the first catheter. The original catheter then is withdrawn over the exchange wire which is maintained in place in the blood vessel. The next succeeding catheter then can be inserted into the patient over the exchange wire.

The foregoing system and technique of using a long exchange wire is not free from difficulty. The proximally extending end of the exchange wire is quite long and cannot be manipulated easily. Typically one member of the medical team involved in the procedure must stand back from the procedure in order to hold the long "tail" (the proximal end) of the guidewire. Additionally, should it be desirable to manipulate the exchange wire, for example, to steer it to a repositioned location, the long trailing end, the exchange wire makes it difficult to manipulate and rotate. Typically, after a catheter exchange has been performed with an exchange wire, the exchange wire is removed and is replaced with a shorter length guidewire that is more easily manipulated by the physician. That, however, adds time and complexity to the procedure.

It would be desirable, therefore, to provide an exchange guidewire that avoided the foregoing difficulties. It is among the general objects of the invention to provide such a guidewire.

SUMMARY OF THE INVENTION

The invention utilizes an exchange length guidewire having proximal and distal segments that are connected to each other in the region of the midpoint of the guidewire by a swivel joint that permits the distal portion of the guidewire to be rotated with respect to the proximal portion. The guidewire, which typically is contained in a coiled tube before use, may be used in a number of protocols including catheter exchanges. Because the distal segment of the guidewire can be rotated freely, without resistance or interference from the proximal, tail segment of the guidewire, the difficulty previously encountered when trying to manipulate and steer a conventional exchange wire is avoided because the proximal tail of the guidewire does not have to be rotated together with the distal portion. Additionally, the proximal segment of the guidewire may be maintained in a coiled-up configuration, within the coiled packing tube that avoids the need for an assistant to support the long proximal tail of a fully extended exchange wire. The swivel joint has an effective diameter that is substantially the same as the proximal and distal segments of the guidewire so that it does not interfere with advancement of the catheter along the guidewire as in a catheter exchange.

It is among the general objects of the invention to provide an improved exchange guidewire.

Another object of the invention is to provide an exchange length guidewire having proximal and distal segments that are connected to each other by a rotatable joint.

Another object of the invention is to provide an exchange guidewire in which the trailing portion of the guidewire can be packaged in a compact configuration that does not interfere with the ability of the distal segment of the guidewire to be rotated and manipulated.

A further object of the invention is to provide an exchange guidewire in which the necessity for replacing the exchange guidewire with a shorter length steerable guidewire may be avoided.

BRIEF DESCRIPTION OF THE DRAWING

The foregoing and other objects and advantages of the invention will be appreciated more fully from the following further description thereof with reference to the accompanying drawings wherein.

DESCRIPTION OF THE PREFERRED EMBODIMENTS

Figure 1:
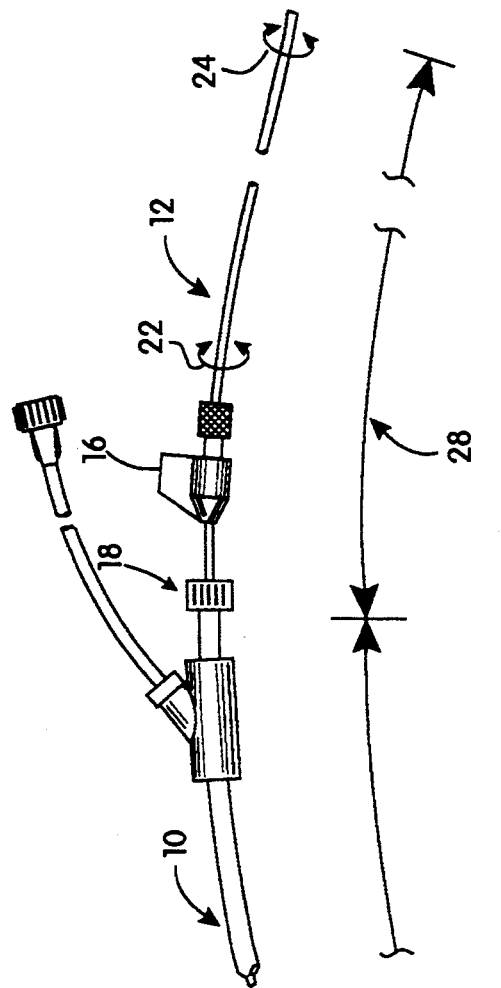
FIG. 1 is a somewhat diagrammatic illustration of a conventional steerable exchange catheter guidewire and catheter illustrating the respective lengths of various sections.
Figure 1:
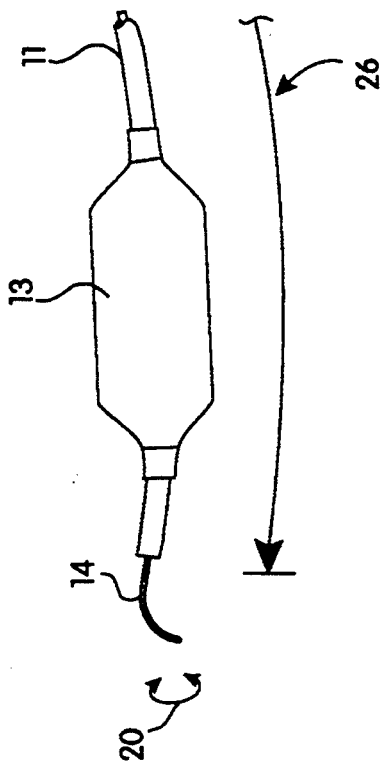

FIG. 1 illustrates the relationship between a catheter 10 and a conventional exchange guidewire 12. The catheter 10 is illustrated as a balloon catheter of the type used commonly in percutaneous transluminal coronary angioplasty procedures. The catheter typically has an elongate flexible shaft 11 and an inflatable balloon 13 mounted to the distal end (the end inside the patient) of the shaft 11. The catheter shaft 11 typically has two lumens (not shown). One lumen communicates the proximal end of the catheter with the interior of the balloon to permit inflation and deflation of the balloon. The other lumen extends the full length of the catheter from the proximal end to a distal outlet tip, distally of the balloon. The other lumen is adapted to receive a guidewire, such as a conventional length guidewire or an exchange guidewire 12. As shown in FIG. 1, the distal tip 14 of the guidewire 12 protrudes beyond the distal end of the catheter and may be formed to include a curve in order to facilitate directional control as the catheter and guidewire arrangement are advanced along the patient's arteries to the intended treatment site. Steering may be facilitated by a clamp 16 that may be attached tightly about the guidewire 12 proximally of the catheter 10. Clamp 16 has a substantially larger diameter than the guidewire and is more easily manipulated and rotated by the physician to transmit rotation to the distal end of the guidewire as suggested by the arrows 22, 24.

In the prior art exchange wires illustrated in FIG. 1, the guidewire shaft is of unitary construction so that in order to rotate the distal end of the guidewire, the entire length of the guidewire must be rotated, including the proximal trailing end as indicated by the arrows 24. Additionally, the extended length that the proximal trailing end of the guidewire requires that an assistant hold the proximal end of a guidewire in order to permit it to rotate as well as to prevent it from becoming kinked or from falling to the floor.

The guidewire may include a variety of constructions such as, for example, the construction illustrated in U.S. Pat. No. 4,545,390 (Leary). In an exchange wire configuration, the proximal shaft of the wire is extended to the approximately 300 cm length of the exchange wire. It will be appreciated that a typical coronary angioplasty catheter will be of the order of 140 cm to 145 cm long. The guidewire may be any convenient diameter, with diameters of the order of 0.014" to 0.018" diameter being conventional. When used with a catheter of the order of 140 cm to 145 cm in length, an exchange wire having a length of about 300 cm will provide adequate exposed portions at all times at the proximal end of the system so that the guidewire can be grasped by a member of the medical team to maintain the position of the guidewire as the catheter exchange is made.

Figure 2:
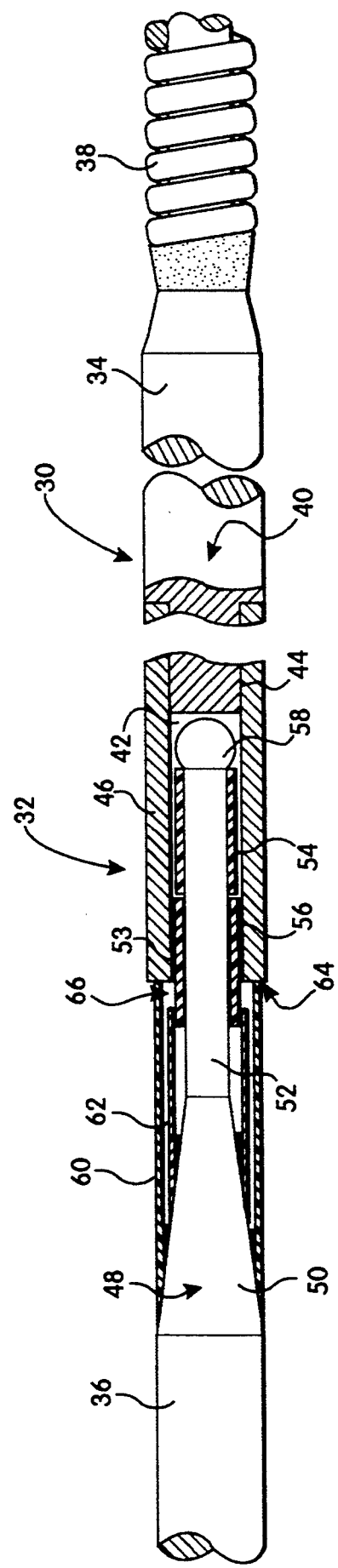
FIG. 2 is an enlarged cross-sectional fragmented illustration of a portion of an exchange guidewire including the joint between guidewire portions according to this invention.

FIG. 2 illustrates one embodiment of an exchange guidewire 30 made in accordance with the invention. In contrast with the prior art exchange guidewires, the guidewire of the present invention is formed to include two distinct segments, including a proximal segment and a distal segment, that are rotatably connected to each other at a swivel joint, indicated generally at 32. Thus, the distal segment 34 of the guidewire can be rotated with respect to the proximal trailing portion 36 of the guidewire. Thus, the distal segment 34 of the guidewire may be rotated to control the orientation of the curved distal tip 14 of the guidewire without requiring that the entire length of the exchange wire, including its proximal portion 36, be rotated. The arrangement provides a number of advantages. Because a substantial proximal length of the guidewire does not have to be rotated together with the distal segment, the drag that the proximal trailing portion of the guidewire normally would impose is avoided. That enhances the sensitivity of the physician to tactile feedback as the guidewire is manipulated in the patient. Additionally, by permitting the distal segment of the guidewire to rotate freely with respect to the proximal segment, it is not necessary to uncoil the entire length of the guidewire until the catheter exchange actually is to be performed. As will be discussed in further detail in connection with the illustration in FIG. 4, that permits the proximal portion of the exchange wire to be maintained in its coiled tubular package, thereby reducing the usual awkwardness in handling such long exchange wires as well as further assuring the sterility of the wire until the time of a catheter exchange.

The distal segment 34 of the guidewire may include a solid shaft having a diameter, for example, of between about 0.014" to 0.018", and a helical coil 38 mounted to the distal end of the shaft. The distal segment of the guidewire may include a construction adapted to facilitate its steerability such as the construction disclosed in U.S. Pat. No. 4,545,390 (Leafy). The distal segment may be considered as a steerable guidewire segment.

FIG. 2 also illustrates the constructional details of the swivel joint. The proximal end 40 of the steerable guidewire 34 in FIG. 2 includes a hollow socket 42. The socket 42 may be formed from a length of stainless steel tubing 46 attached to the proximal end 40 of the shaft of the distal segment 34. The proximal end of the steerable segment 34 may be machined as by centerless grinding, to form a narrower diameter pin 44 that is inserted into and is attached to tubing 46. The tubing 46 may be joined to the shaft by welding or other suitably strong adhesion method depending upon the materials utilized for the tubing 46, which may include any suitable rigid biocompatible material.

The distal end 48 of the trailing proximal segment 36, which may also be a stainless steel shaft, is ground to a taper 50 and a distally extending cylindrical segment 52 of a diameter adapted to be inserted in the steerable guidewire socket 42. The outer diameter of the cylindrical segment 52 and the inner diameter of the tubing 46 define sufficient annular clearance to receive a pair of tubular sleeves 54, 56. The sleeves 54, 56 preferably are formed from polyimide tubing. The proximal sleeve 56 is adhesively attached, as at 53, to the inner surface of the socket 42 while the more distal of the sleeves 54 may be adhesively attached to the surface of the cylindrical segment 52. A suitable adhesive may be, for example, an epoxy or cyanoacrylate.

The annular clearance between the end segment 52 and tube 46 and the wall thickness of the polyimide tubes 54, 56 are such as to permit the distal steerable segment 34 to be freely rotatable with respect to the proximal trailing segment 36. By way of example, in a guidewire having an outer diameter of the order of 0.014", the outer diameter of the distal polyimide sleeve 54 may be of the order of 0.0085" and the inner diameter of the tubing 46 may be of the order of 0.010". As to the clearance between the cylindrical segment 52 and the proximal sleeve 56, the outer diameter of cylindrical segment 52 may be 0.0055". The inner diameter of the proximal polyimide sleeve 54 may be of the order of 0.007". From the foregoing, it will be appreciated that the sleeves 54, 56 cannot telescope, one within the other, and their ends will abut when brought together. Therefore, the proximal and distal segments 36, 34 cannot be separated axially.

An additional retaining element in the form of a tip ball 58 may be welded or otherwise formed on the distal end of the cylindrical segment 52 to prevent the distal sleeve 54 from pulling free even under tensile loads. The tip ball 58 should have a diameter greater than the inner diameter of the distal sleeve 54 but smaller than that of the socket 42. In the dimensional example of an exchange wire having an outer diameter of 0.014", the tip ball may have a diameter of the order of 0.0085".

Because the distal end of the proximal guidewire section 36 is of reduced diameter, it may be desirable to enhance the stiffness of that region in order to reduce the risk of the guidewire becoming bent or kinked in that region. In order to reinforce the joint of FIG. 2 a pair of thin wall, relatively stiff tubes, such as polyimide tubes 60, 62 may be disposed concentrically between the tapered portion 50 of the proximal segment 36 and the proximal end 64 of the tube 46 of the distal section 34. The tubes 60, 62 may be attached at their proximal ends to the tapered portion 50 of the end segment 52 by a suitable adhesive, such as cyanoacrylate. The distal ends of the tubes 60, 62 should remain unattached to proximal tube 46 of the distal section 34. The outer reinforcing tube 60 lightly abuts the proximal end 64 of the tube 46 to enhance the axial column strength of the joint during axial compressive loads. The diameter of outer tube 60 is approximately equal to but is no greater than the outer diameter of other portions of the guidewire. The tube 60 thus also bridges the otherwise reduced diameter region at the joint to create a smoother transition between the proximal and distal sections 36, 34.

The second, inner tube 62 is concentric with the outer reinforcing tube 60 and provides further reinforcement for the swivel joint in the event that the stiffness of the outer tube 60 is overcome and outer tube bending occurs. The distal end of the inner tube 62 preferably is spaced slightly from the end wall 64 of the tube 46 and, thus, only contacts the end wall 64 if some bending occurs. Upon contact, the inner tube 62 enhances the compressive strength to the structure resisting further bending at the joint. The spacing 66 (exaggerated in FIG. 2) between the tube and socket end wall 64 may be set so that the edge of the inner tube 62 strikes the end wall 64, as the joint bends, at a point that is well before the elastic limit of the elongated end segment 52.

By way of further dimensional example a 0.014" exchange wire the tube 46 of the proximal end of the distal section 34 may be of the order of 2 cm long having an outer diameter of 0.014" and an inner diameter of 0.010". The proximal and distal sleeves 56, 54 may have a wall thickness of the order of 0.00075" and lengths of a few millimeters or more. The length of the tapered segment 50 of the proximal section 36 preferably is at least about 1 cm.

Figure 3:
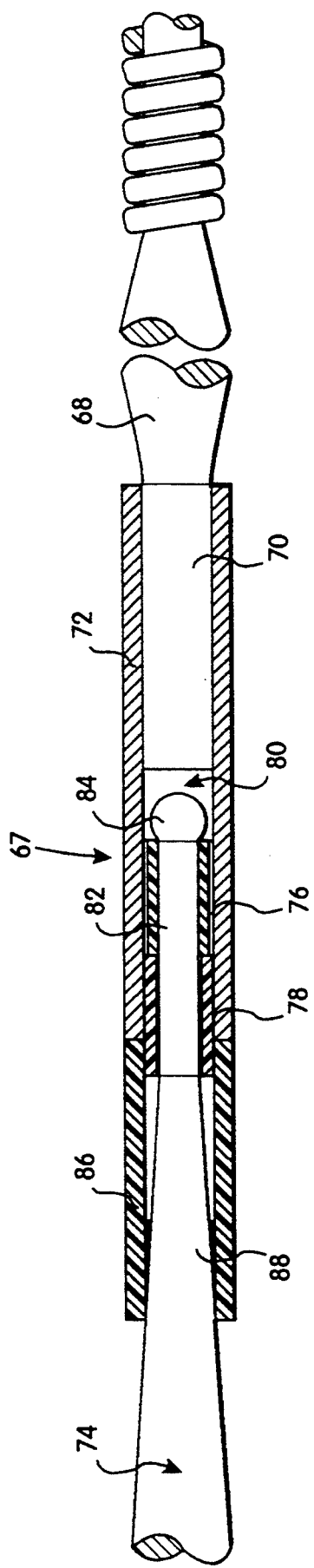
FIG. 3 is an enlarged cross-sectional view of an alternative embodiment of a rotatable joint in an exchange guidewire according to this invention.

FIG. 3 illustrates another embodiment of a swivel joint 67 of the invention. In this embodiment the proximal end 70 of the shaft of the steerable guidewire section 68 is reduced in diameter, as by centerless grinding. A tube 72 that may be stainless steel is attached to the proximal end 70. The proximal trailing section 74 of the guidewire, as that of the FIG. 2 embodiment, includes a pair of retention sleeves 76, 78, the proximal of which (78) is cemented to the socket 80 while free to rotate relative to the end segment 82. The distal sleeve tubes 76 is cemented to the end segment 82, free to rotate relative to the socket 80. A tip ball 84 also is attached to the end of the end segment subsequent to mounting the sleeve tubes 76, 78 thereon.

In the embodiment of FIG. 3 only one reinforcing tube 86 is used to strengthen the swivel joint. The tube 86 preferably is formed from polyimide and has a greater wall thickness than that of the embodiment of FIG. 2. For example, the reinforcing tube 86 may have a wall thickness of about 0.00175". The tube 86 may be several millimeters or more in length. The tube 86 is adhesively attached to the tapered portion 88 of the end segment 82 and is free to rotate relative to the socket 80 and proximal disposed sleeve 78. The use of a single reinforcing tube of sufficient strength simplifies the overall construction of the swivel joint without unduly sacrificing bend resistance.

Figure 4:
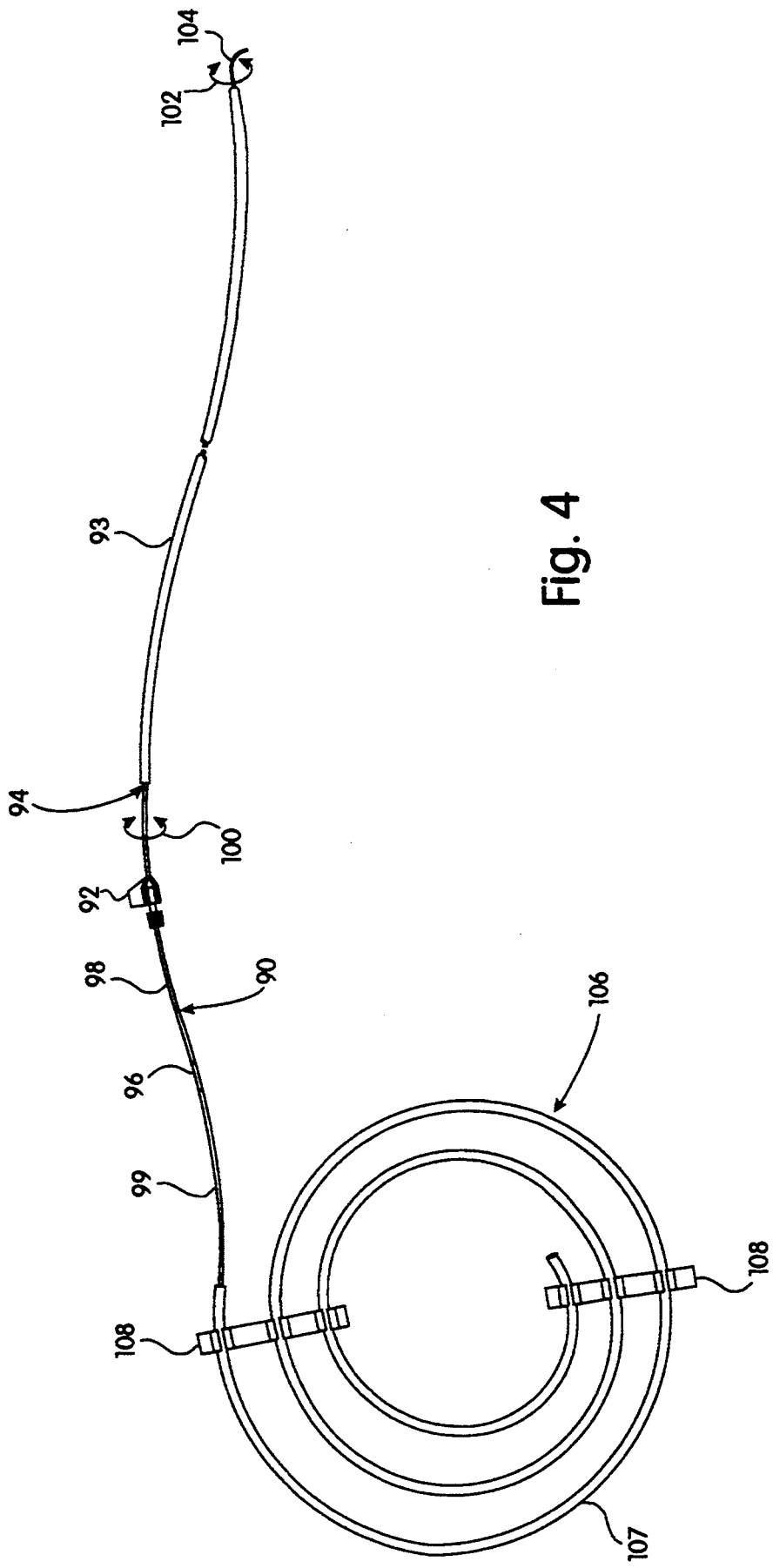
FIG. 4 is a somewhat diagrammatic illustration of the exchange guidewire of either FIGS. 2 or 3 mounted in a catheter and illustrating the steering of the catheter while the trailing end is stored in a compacted, protected configuration.

FIG. 4 illustrates the manner in which a swivel exchange guidewire 90 according to this invention may be used. A steering clamp 92 is placed about the guidewire 90 proximally of the catheter 93 end 94 and distally of the swivel joint 96. The distal steerable portion 98 of the guidewire 90 rotates as shown (arrows 100, 102) causing the steerable tip 104 to rotate. The swivel joint 96 allows the trailing portion 99 of the guidewire, however, to remain stationary during simultaneous rotation of the steerable guidewire 98. As such, the trailing portion 99 may be stored in, for example, a packaging hoop 106 by means of a large diameter tube 107 held in a coil with frames 108 as shown. The trailing portion 99 thus may be conveniently held in a sterile environment without need of an assistant to stand far behind the physician to support the trailing end. Additionally, by means of the swivel joint 96, the packaging hoop-stored trailing portion 99 exerts no drag on the distal steerable guidewire 98, facilitating ease of steering.

When a catheter exchange is desired, an assistant may quickly withdraw the trailing portion of the guidewire from the storage hoop 106 and extend the trailing portion 99 out to its full length. The steering clamp 92 is then removed and the catheter 93 is withdrawn from the patient, over the exchange wire, while at all times maintaining a firm grip upon some portion of the guidewire 90 at either its steerable 98 or trailing 99 portions. Since the joint 96 is relatively smooth and no wider in diameter than the remainder of the steerable 98 or trailing 99 guidewire portions, the catheter 93 slides smoothly over it without interference.

After the first catheter is removed, a second catheter is advanced over the exchange wire and is guided by the wire to the treatment site in the patient's arteries. After the second catheter has been positioned, the trailing portion of the guidewire may be rethreaded into its storage hoop 106 so as to be retained in an out of the way, compact configuration as the procedure continues. It will be appreciated because a distal portion of the guidewire is independently rotatable with respect to the proximal portion, the physician may find it unnecessary to remove the exchange wire and replace it with a conventional, shorter length steerable guidewire.

Thus, it will be appreciated that the invention provides an improved exchange wire adapted particularly for use in angioplasty and, especially, percutaneous transluminal coronary angioplasty. The invention provides a means by which a catheter exchange may be effected by using an exchange guidewire but in which the awkwardness associated with handling of the lengthy trailing portion of the guidewire is avoided.

It should be understood, however, that the foregoing description of the invention is intended merely to be illustrative thereof and that other embodiments, modifications and equivalents may be apparent to those skilled in the art without departing from its spirit.

Having thus described the invention what I desire to claim and secure by Letter Patent is:

1. An exchange guidewire for use with a catheter in a percutaneous transluminal coronary angioplasty procedure comprising:
   an elongate, flexible, proximal, trailing guidewire section having proximal and distal ends;
   an elongate, flexible, distal, steerable guidewire section having proximal and distal ends, said steerable guidewire section having a length substantially similar to that of a conventional length guidewire;
   the proximal end of the distal section being rotatably connected to the distal end of the proximal section, wherein the distal end of the trailing guidewire rotatably connected to the proximal end of the steerable section includes an end segment having a substantially smaller outer diameter than more proximal disposed portions of the guidewire, the proximal end of the steerable guidewire section including a longitudinally disposed hollow socket for accepting the smaller Outer diameter end segment of the distal end, and
   a bridging tube disposed at the joint between the trailing guidewire and the steerable guidewire, and having an outer diameter smaller than or substantially equal to the outer diameter of the trailing guidewire to cover the end segment longitudinally between the trailing guidewire and the proximal end of the steerable guidewire;
   said trailing guidewire section being of such length that the combined length of proximal and distal guidewire sections is that of an exchange wire for facilitating exchange of catheters, and
   means for removably storing the trailing guidewire section in a coiled, stored configuration,
   whereby the distal guidewire section may be rotated and manipulated while within a patient without rotating the stored proximal trailing guidewire section which may later be unstored to allow a catheter exchange.

2. An exchange guidewire as defined in claim 1 further comprising a sleeve having a lumen of substantially equal inner diameter to the outer diameter of the end segment of the trailing guidewire, the end segment being rotatably disposed within the sleeve and the sleeve being fixedly joined to the hollow socket.

3. An exchange guidewire as defined in claim 2 wherein the end segment of the trailing guidewire includes, disposed distally of the sleeve, a larger diameter stop segment fixedly joined thereto to prevent axial displacement of the trailing guidewire away from the steerable guidewire.

4. An exchange guidewire as defined in claim 3 wherein the stop segment comprises a second sleeve and an enlarged diameter ball weld located upon a most distally disposed tip of the end segment.

5. An exchange guidewire as defined in claim 1 wherein the bridging tube is fixedly joined to the trailing guidewire and rotatably abuts the proximal end of the steerable guidewire.

6. An exchange guidewire as set forth in claim 5 further comprising an inner tube having a smaller outer diameter than the inner diameter of the bridging tube disposed upon the segment along the joint between the trailing guidewire and the steerable guidewire and fixedly joined to the end segment of the trailing guidewire for enhancing bending strength of the joint.

7. An exchange guidewire comprising
   a steerable guidewire section having a proximal and a distal end;
   a trailing guidewire section having a proximal end and a distal end and being of substantially equal to or smaller outer diameter than the steerable guidewire section; and
   means for freely and rotatably joining the proximal end of the steerable guidewire section to the distal end of the trailing guidewire section in alignment longitudinally with one another so as to limit axial movement between the steerable guidewire section and trailing guidewire section, the means for rotatably joining said sections extending radially outwardly no further than the outer diameter of the guidewire sections, said rotatable means comprising a trailing guidewire end segment having a substantially smaller outer diameter than more distal portions of the guidewire, a longitudinally disposed hollow socket on the proximal end of the steerable guidewire section for accepting smaller outer diameter end segment, a sleeve having a lumen of substantially equal inner diameter to the outer diameter of the end segment of the trailing guidewire, the end segment being rotatably disposed within the sleeve and the sleeve being fixedly joined to the hollow socket, wherein the end segment of the trailing guidewire section includes distally of the first sleeve a second sleeve fixedly joined thereto to prevent axial displacement of the trailing guidewire segment away from the steerable guidewire segment.

8. The exchange guidewire according to claim 7 including means for removably storing the trailing guidewire section in a coiled, stored configuration, whereby the steerable guidewire section may be rotated and manipulated while within a patient without rotating the coiled, trailing guidewire section and may be unstored later to allow a catheter exchange.

* * * * *